(12) United States Patent
Trudel et al.

(10) Patent No.: US 9,572,966 B2
(45) Date of Patent: Feb. 21, 2017

(54) CLEANSING DEVICE AND METHOD

(71) Applicants: Lynda Trudel, Stouffville (CA); Chantal Jones, Stouffville (CA); Olivia Jones, Stouffville (CA)

(72) Inventors: Lynda Trudel, Stouffville (CA); Chantal Jones, Stouffville (CA); Olivia Jones, Stouffville (CA)

(*) Notice: Subject to any disclaimer, the term of this patent is extended or adjusted under 35 U.S.C. 154(b) by 475 days.

(21) Appl. No.: 13/970,829

(22) Filed: Aug. 20, 2013

(65) Prior Publication Data
US 2014/0058342 A1   Feb. 27, 2014

Related U.S. Application Data

(60) Provisional application No. 61/691,474, filed on Aug. 21, 2012.

(51) Int. Cl.
*A61M 35/00* (2006.01)
*A61F 6/06* (2006.01)
*A47K 7/08* (2006.01)

(52) U.S. Cl.
CPC .............. *A61M 35/003* (2013.01); *A47K 7/08* (2013.01)

(58) Field of Classification Search
CPC ........................... A61M 35/00; A61M 35/003
See application file for complete search history.

(56) References Cited

U.S. PATENT DOCUMENTS

| | | | |
|---|---|---|---|
| 2001/0003565 A1* | 6/2001 | McOsker | A45D 40/00 401/132 |
| 2002/0026140 A1* | 2/2002 | McNamara | A61F 13/2051 604/12 |
| 2002/0127192 A1* | 9/2002 | Murphy | A61K 8/02 424/64 |

* cited by examiner

Primary Examiner — Philip R Wiest
Assistant Examiner — Sara Sass
(74) Attorney, Agent, or Firm — Aird & McBurney LP

(57) ABSTRACT

An external device for applying a substance to the perineum comprises: a bottom wall; and an elastic side wall extending from the bottom wall; wherein said bottom wall and side wall together form an open cup-shaped body for holding the substance.

20 Claims, 4 Drawing Sheets

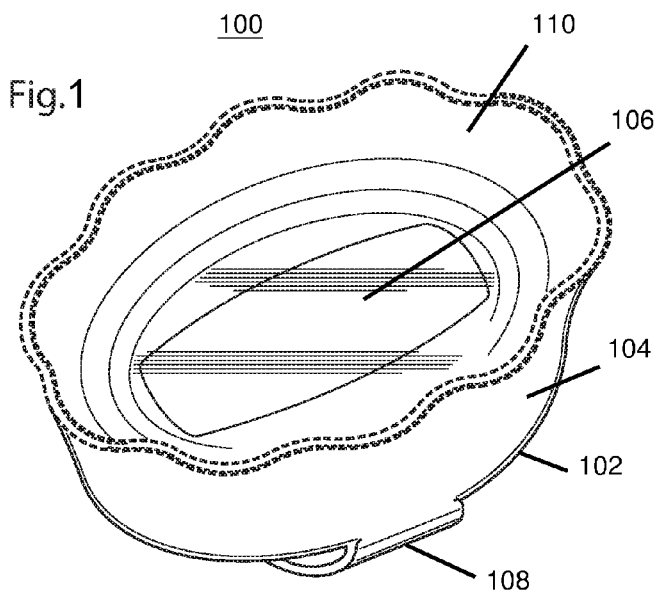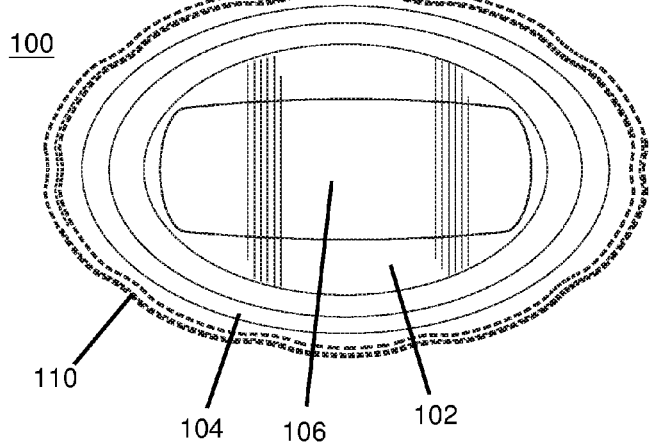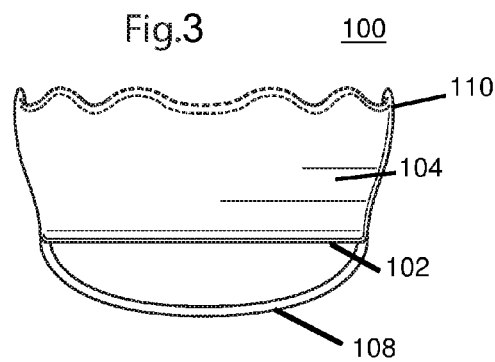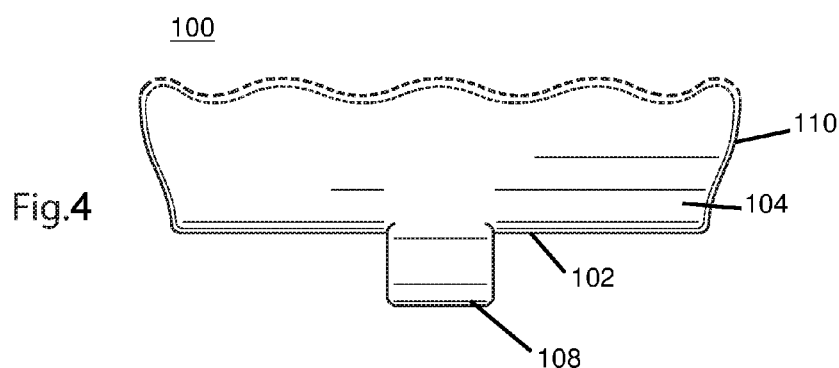

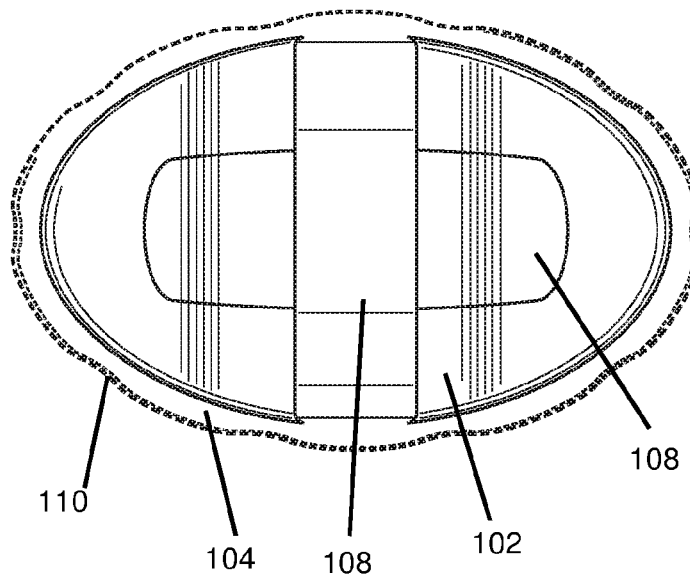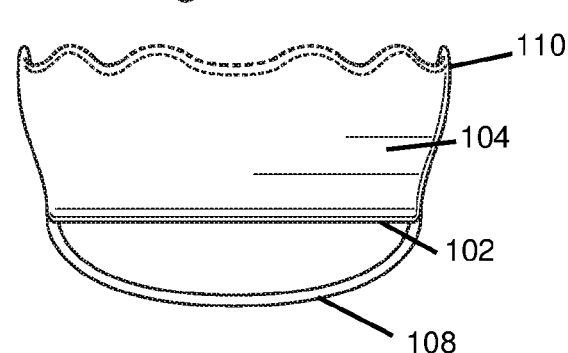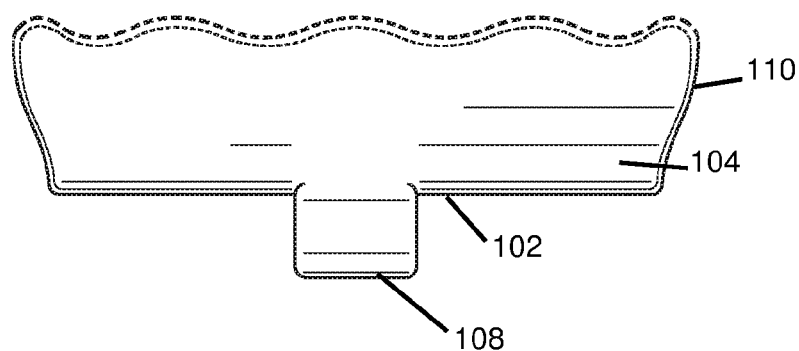

US 9,572,966 B2

CLEANSING DEVICE AND METHOD

CROSS-REFERENCE TO RELATED APPLICATIONS

This application claims the benefit of U.S. Provisional Application No. 61/691,474 filed Aug. 21, 2012. The disclosure of the above-referenced application is fully incorporated herein by reference.

FIELD OF THE INVENTION

The present invention relates to personal hygiene. More specifically, the present invention relates to a device and method for cleansing the perineum and/or for applying a substance to the perineum.

BACKGROUND OF THE INVENTION

Methods of cleaning the perineum are known, including using a washcloth, water cupped in the hands, or douching. Additionally, it is known to crouch down in front of a tap and splash the water onto the perineum. However, such methods have drawbacks. For example, if a woman is menstruating, the use of a washcloth is generally not desired because of staining that could occur. Cupping water in the hands or crouching in front of a tap is awkward and requires direct contact between the hands and the perineum, which may not be desired in a daycare or healthcare setting. Additionally, if a woman is menstruating or has an infection, she may not wish to directly touch her perineum. Finally, douching has many drawbacks, including disruption of the natural flora and the pH of the vaginal microenvironment. An example of a device for douching is described in U.S. Pat. No. 7,186,243. To date, there is no known tool or device available for cleaning the perineum.

Therefore, although there are many methods for cleaning the perineum, there is still a need to identify alternative approaches.

SUMMARY OF THE INVENTION

In accordance with an aspect, there is provided an external device for applying a substance to the perineum, the device comprising:
  a bottom wall;
  an elastic side wall extending from the bottom wall;
  wherein said bottom wall and side wall together form an open cup-shaped body for holding the substance.

In an aspect, the bottom wall is elastic.

In an aspect, the bottom wall contains a region of increased elasticity as compared to the remainder of the bottom wall.

In an aspect, the region of increased elasticity is formed a portion of the bottom wall that has a reduced thickness as compared to the remainder of the bottom wall.

In an aspect, the region of increased elasticity is formed from a material that is different from the material from which the remainder of the bottom wall is formed.

In an aspect, the region of increased elasticity and the remainder of the bottom wall are integrally formed.

In an aspect, the bottom wall and side wall are integrally formed.

In an aspect, the side wall is collapsible.

In an aspect, an upper edge of the side wall is flat.

In an aspect, an upper edge of the side wall is scalloped or ruffled.

In an aspect, an upper edge of the side wall is formed from a plurality of pointed arches.

In an aspect, the device further comprises a member coupled to the cup-shaped body for holding the device.

In an aspect, the member is a strap that is coupled to the opposing sides of the bottom wall and/or side wall and thereby passes across the outside of the bottom wall.

In an aspect, the strap is sized to hold one or more fingers of a user against the bottom wall.

In an aspect, the cup-shaped body is sized to cover the perineum.

In an aspect, the cup-shaped body is sized to cover one of the anus and the vulva.

In an aspect, the device in use does not form a seal with the perineum.

In an aspect, the device further comprises a handle.

In an aspect, the handle is removable.

In an aspect, the substance is water, lotion, cream, ointment, or paste.

In an aspect, the substance is water.

In an aspect, the device is made at least in part from an elastomeric material selected from the group consisting of silicone, polyurethane, copolymers of silicone and polyurethane, polyolefins, such as polyisobutylene and polyisoprene, neoprene, nitrile, vulcanized rubber and combinations thereof.

In an aspect, the device is made from silicone.

In an aspect, the side wall and/or the bottom wall is smooth.

In accordance with another aspect, there is provided a method for applying a substance to the perineum, the method comprising:
  depositing the substance into the cup-shaped body of the device described herein; and
  using the device to apply the substance to the perineum.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DESCRIPTION OF THE FIGURES

The present invention will be further understood from the following description with reference to the Figures, in which:

FIG. 1 shows a perspective view of the device described herein;

FIG. 2 shows a top plan view of the device of FIG. 1;

FIG. 3 shows a front elevation view of the device of FIG. 1;

FIG. 4 shows a side elevation view of the device of FIG. 1;

FIG. 5 shows a bottom plan view of the device of FIG. 1;

FIG. 6 shows a back elevation view of the device of FIG. 1;

FIG. 7 shows a side elevation view of the device of FIG. 1;

DETAILED DESCRIPTION OF THE INVENTION

Figure 8:
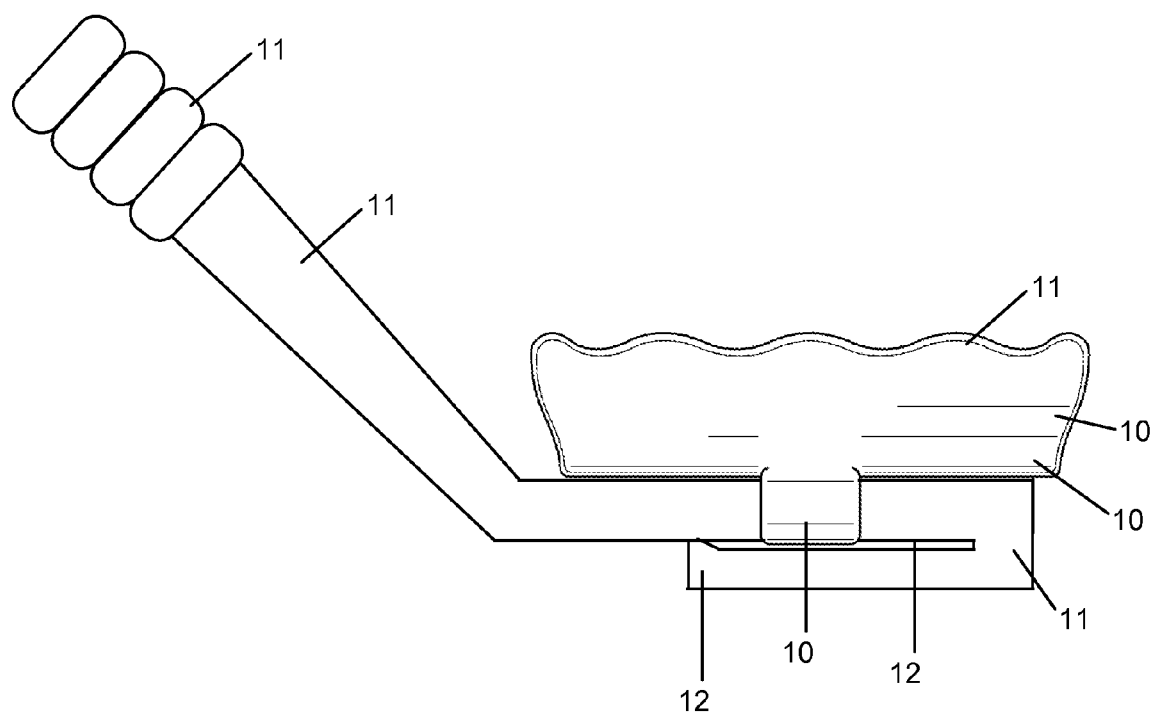
FIG. 8 shows a side plan view of the device of FIG. 1 coupled to a handle.

Conventional methods of cleaning the external perineal region, including the vulva and the anus, involve using a washcloth or cupping water in the hands and then splashing that water on the region to be cleaned. Douching is also used in order to clean internally, but this is not advised as it can disrupt the natural microenvironment of the vagina.

Described herein is a novel device and method for cleaning the external structures of the perineum, including the anus and the vulva. The device is in an aspect reusable and therefore environmentally friendly. In other aspects, the device is easily cleanable and provides a barrier between the user's hand and the perineal structures.

The device may be provided with an accessory handle that allows use by pregnant or obese users, who often have difficulties in reaching and therefore sufficiently cleaning the perineum.

In an aspect, the device does not sealingly engage the body when applied to the perineum and therefore mitigates the production of suction or a vacuum between the device and the vagina, for example. Additionally, because of the lack of sealing engagement between the device and the body, water or another substance within the device is not forced up into the vagina. Accordingly, the device is, in an aspect, used to clean the external surfaces and folds of the vulva and/or anus thoroughly without introducing substantial amounts of water or cleanser into the delicate vaginal environment.

The device can be used to promote proper cleansing techniques amongst all age groups and is suitable for use in daycare or healthcare settings, as well as in the home for personal hygiene uses. It provides a barrier between the user and the perineum, and thereby mitigates transfer of bacteria, microbes, or other substances between the fingers and the perineum. In this way, the device protects the perineum from germs on the user's fingers and also protects the users fingers from germs found on the perineum.

The device can be used and cleaned for reuse. It is suitable for daily use, during menstrual cycles, during or after pregnancy, or after sexual intercourse to reduce unwanted odours and chance of infection. To this regard, it can be used to clean the perineum with water or another cleanser or it can be used to apply a substance, such as a vaginal or haemorrhoid cream, to the perineum while eliminating the need to touch the perineum directly.

Turning now to FIGS. 1 to 7, the device 100 is for external use and is generally cup-shaped. The device 100 comprises a bottom wall 102 and a side wall 104 extending upwardly from the bottom wall. The bottom wall 102 and side wall 104 are flexible and elastic, meaning that they can easily resume their original shape after being stretched or bent. Typically, the bottom wall 102 and side wall 104 are integrally formed from a single piece of silicone.

The device 100 is typically round or ovoid in cross-section so that there is only a single continuous side wall 104. This reduces the number of corners or crevices in which bacteria or other microbes could grow and makes cleaning the device a simple task. However, it will be understood that the shape is not limiting and the device could instead have a polygonal cross-section. What is important is that the device 100 be capable of holding a liquid or other material for application to the perineal region. Typically, the device 100 holds water when it is being used for cleaning the perineum. The side wall 104 is collapsible so that when the device 100 is applied to the perineum with sufficient pressure, the side wall 104 flexes and collapses, thereby actively splashing the water against the region to be cleaned.

Turning now to FIGS. 1, 2, and 5, the bottom wall 102 is shown as having a region of increased elasticity 106 as compared to the remainder of the bottom wall 104. The region of increased elasticity 106 is typically integrally formed with the remainder of the bottom wall 104 and has a reduced thickness as compared to the remainder of the bottom wall 104. Due to the reduced thickness the region of increased elasticity 106 will be easier to deform than the remainder of the bottom wall 104. The region of increased elasticity 106 allows a user to stretch the bottom wall 104 in order to move the water around inside of the device 100 and thereby cleanse the perineal region. Furthermore, if the device 100 is being used to clean the vulva, the user can stretch the region of increased elasticity 106 and then gently open the labia for cleansing with the water in the device 100 without touching the vulva directly.

The illustrated device also comprises a member 108 that is used to more easily hold and control the device 100. The member 108 is typically a strap that is coupled to opposing sides of the bottom wall 102 and/or side wall 104 and thereby passes across the outside of the bottom wall 102.

The member 108 is typically sized to hold one or more fingers of a user against the bottom wall 102. As is shown in the figures, the member 108 runs perpendicularly to the region of increased elasticity 106. In this way, when three fingers, for example, are inserted between the member 108 and the bottom wall 102, the two side fingers can be used to support the bottom wall 102 while the middle finger stretches the region of increased elasticity 106 and thereby swishes the liquid around inside the device 100 and/or opens the labia as described.

Like the region of increased elasticity 106, the member 108 is typically formed integrally with the remainder of the device 100. This creates a seamless device that has fewer cracks and crevices in which bacteria and microbes may grow.

As is shown in FIG. 1, the side wall 104 of the device 100 has an uneven or ruffled upper edge 110. By making the upper edge 110 uneven, the device is discouraged from forming a seal or vacuum against the perineum. This allows the water to flow and splash around freely inside the device 100 without forcing the liquid into the vagina or anus or creating undesirable suction.

The device 100 may be sized to cover and clean the entire perineum at once or it may be sized to cover only one of the anus and the vulva. If the device is sized to cover only one of the anus and the vulva it will advantageously keep these two regions separate and thereby discourage transfer of harmful bacteria or microbes from the anus to the vulva and vagina. In a typical aspect, the device 100 is sized to hold about 100 ml of water.

Figure 9:
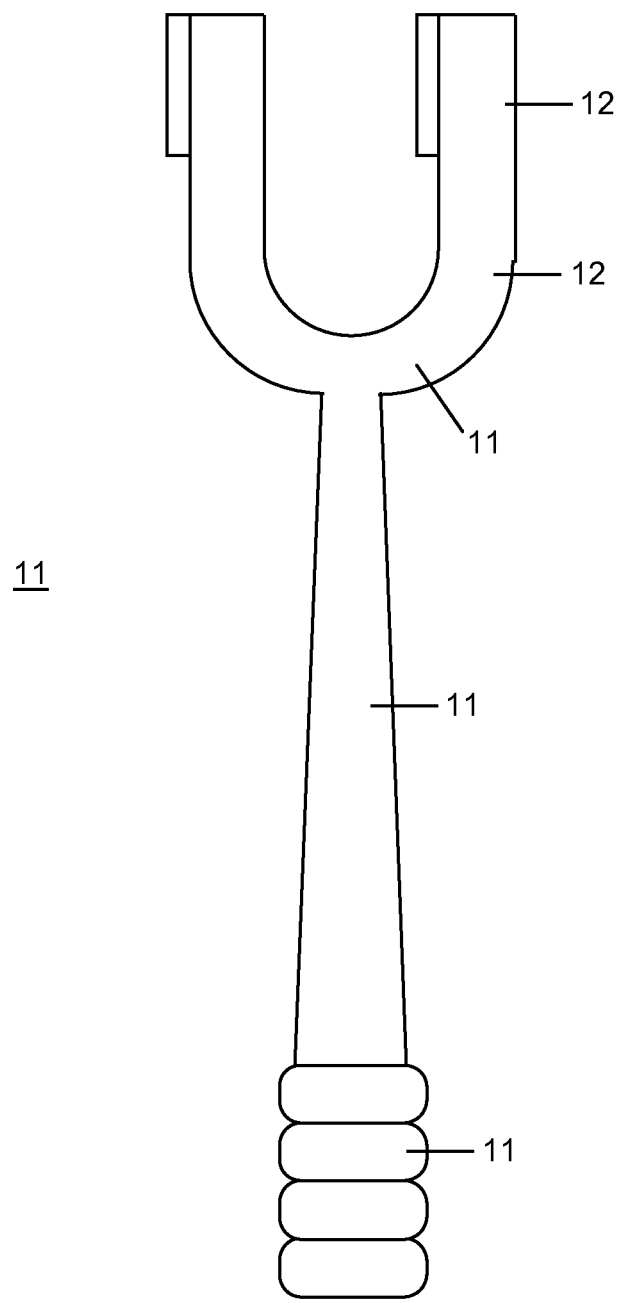
FIG. 9 shows a top plan view of the handle of FIG. 8 in isolation.

Turning now to FIGS. 8 and 9, a removable handle 112 for attaching to the device 100 is shown. The handle 112 advantageously extends the reach of the device 100 and is for use by people who are pregnant, overweight, or for other reasons have difficulties in reaching the perineal region without such a handle 112.

The handle 112 has a grip 114, an extension arm 116, and a connector 118 for coupling the handle 112 to the device 100. The connector 118 typically has a pair of parallel arms 120 that fold over upon themselves to form a slot 122 into which the member 108 is inserted. By forming the connector 118 from a pair of parallel arms 120, the region of increased elasticity 106 is still accessible. It will be understood, however, that the connector 118 could instead have a single arm 120 that would cover the region of increased elasticity 106 as a person requiring the use of the handle 112 would not likely be capable of using a finger to stretch the region of increased elasticity 106. The handle 112 could also be integrally formed with the device 100 instead of being removable, as shown.

Although the device 100 has been described above in detail as being for use in cleaning the vulva, it will be evident that the device could be used by both males and females and could be used to clean or apply a substance to the anus of either males or females. The device is also suitable for veterinary purposes, such as for cleansing or applying creams to the perineum of domestic animals. Additionally the device could be used as a barrier for expressing the anal sacks of animals such as ferrets and dogs. Furthermore, the device is suitable for use in the collection of urine or stool samples in a simple and hygienic manner.

The bottom wall 102 has been described above as being elastic, however, it will be understood that the bottom wall need not be elastic. It could, for example, be made from a rigid material that is coupled to the elastic material of the side wall 104.

The elastic material used to form the side wall 104 and/or the bottom wall 102 can be any material that is reversibly deformable. Examples include silicone, polyurethane, copolymers of silicone and polyurethane, polyolefins, such as polyisobutylene and polyisoprene, neoprene, nitrile, vulcanized rubber and combinations thereof. It is generally desirable that the material chosen for use be hypo-allergenic, as the device is intended for use near the perineum, which is a delicate area of the body. Likewise, the material chosen is desirably easy to clean with soap and water and does not promote the growth of bacteria or other microbes. Thus, silicone is a typical choice.

The region of increased elasticity 106 has been described above as being made from same material as the bottom wall 104, but simply having a reduced thickness so that the elasticity is increased in the desired region. However, it will be understood that the region of increased elasticity 106 could be made from a different material from the remainder of the bottom wall 104. For example, the bottom wall 104 could be made from a generally rigid plastic having an insert made from an elastic material such as silicone, with the insert forming the region of increased elasticity 106. In another example, the bottom wall 104 could be made from an elastic material and the insert could be made from a material that has a greater elasticity than that of the material from which the bottom wall 104 is made.

The upper edge 110 can be of any desired shape, including a flat shape. However, it is typically uneven as illustrated. The upper edge 110 may be, for example, scalloped, ruffled, or formed from a plurality of pointed arches. In an aspect, the upper edge 110 is shaped to resemble the petals of a flower, creating a pleasing aesthetic design along with a functional advantage of avoidance of creating a vacuum or suction, as has been described.

The device 100 is also typically formed with a smooth side wall 104 and bottom wall 102 without any apparent ridges or depressions within the surface. Of course, it will be understood that ridges, bumps, or depressions could be provided as desired on one or all parts of the device. For example, the outside surface of the bottom wall 102 may be provided with ridges or bumps to increase frictional contact with the user's fingers or hand. Similar structures may be found on the surface of the member 108 where contact is made with the fingers or hand of the user. In a typical aspect, 3 horizontal ridges are included on each side of member 108 to improve gripping stability.

In use, a user in the shower or sitting over a toilet or bathtub, for example, holds the device 100 by inserting three fingers into the space between the member 108 and the bottom wall 102. The user then fills the device 100 with water and glides the device between the legs so that the device 100 directs the water to the perineum as a whole, or the anus or vulva as desired. The device 100 can be pressed against the perineum and typically does not form a vacuum or any great degree of suction due to the uneven shaping of the upper edge 110 of the side wall 104. The application of force will encourage the side wall 104 to collapse, thereby splashing water within the device 100 and bringing it closer to the perineum. The user then freely stretches the region of increased elasticity 106 with one of his or her fingers thereby agitating the water within the device 100 and cleaning the perineum. The device 100 can be easily refilled with water as desired until the perineum is clean. The device 100 can then be washed, for example with warm, soapy water, and left to dry so that it will be ready for its next use.

The device 100 has been described above as being for use in cleansing the perineal region. However, the device 100 could also be used in many different ways. For example, the device 100 is used to apply various vaginal creams by depositing the cream into the cup-shaped body in the area of the region of increased elasticity 106 and then applying the cream to the vulva by stretching the region of increased elasticity 106 with a finger. In another example, the device 100 is used to apply haemorrhoid cream to the anus of a male or female user. This prevents the need to directly touch the anus and also therefore prevents transfer of any bacteria from the hands to the anus and vice versa. In yet another example, the device 100 could be used when changing diapers in order to apply diaper cream or cleanse the perineum of a baby.

Thus, it will be evident that the device 100 is particularly well-suited to use in daycare or healthcare settings where the person using the device 100 is a daycare or healthcare provider and the device 100 is being used on the perineum of a baby during diaper changes, for example, or a patient. This is because the device 100 provides a reusable barrier between the user and the baby or patient. Thus, transfer or bacteria or microbes from the fingers or under the fingernails is avoided and an increased level of comfort is afforded to the user and the child, the child's parents, or the patient.

In order to facilitate the application of creams, the device 100 may be turned completely inside-out to allow the region of increased elasticity 106 to be exposed, making it easier to apply the cream to any desired area. To turn the device 100 inside-out, the side wall 104 is simply collapsed or folded down thus exposing the region of increased elasticity 106.

Furthermore, as the device is typically made of a durable material such as silicone, it is in an aspect reusable and washable. In this way, the device 100 is environmentally friendly. The device 100 could be provided with a region for writing a name with an indelible marker, for example, so that if it was used in a daycare or healthcare setting each baby or patient could have a device 100 designated for his or her own specific use. This would help mitigate the waste associated with wearing a new pair of disposable gloves each time a different baby is being diapered, as the barrier between the user and the baby is being provided by a reusable device 100 rather than disposable plastic gloves.

The device could also be used by a mother after delivering a baby to gently cleanse the perineum. This region is generally quite tender following a vaginal birth and the device could therefore be used to apply water or other agents, such as witch hazel, to the tender area. In a similar manner, the device could be used in helping treat or clean the anus when afflicted with haemorrhoids.

The device 100 could also be made as a single-use device 100. It could be provided sterilized and pre-packaged so that a new device 100 could be used each time it is desired. In this aspect, generally the device 100 would be made from a material that is less expensive and perhaps less durable, as it is not intended for more than one use.

The device 100 has been described above as having a volume of about 100 ml. However, it will be understood that the volume and other parameters can be varied depending upon the intended use of the device 100. For example, the device could be designed to have a much smaller volume if it is being used to apply diaper cream to babies. It could be designed to have a much larger volume if it is being used to cleanse the perineum of a plus-sized person. It will also be understood that the device could be used to apply more than just water to the perineum. For example, it could be used to apply any of a variety of creams, lotions, ointments, pastes, and so on. Such substances could include medications or other ingredients. Furthermore, when the perineum is being cleaned, water alone could be used or any known personal cleansing solution could be used instead or could be added to the water.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The above disclosure generally describes the present invention. Although specific terms have been employed herein, such terms are intended in a descriptive sense and not for purposes of limitation.

All publications, patents and patent applications are herein incorporated by reference in their entirety to the same extent as if each individual publication, patent or patent application was specifically and individually indicated to be incorporated by reference in its entirety.

Although exemplary embodiments of the invention have been described herein in detail, it will be understood by those skilled in the art that variations may be made thereto without departing from the spirit of the invention or the scope of the appended claims.

The invention claimed is:

1. An external device for applying a substance to the perineum, the device comprising:
 a bottom wall;
 an elastic side wall extending from the bottom wall, wherein an upper edge of the side wall is scalloped or ruffled such that, in use, a vacuum is not formed between the device and the perineum;
 wherein said bottom wall and side wall together form an open cup-shaped body for holding the substance; and
 wherein the bottom wall contains a region of increased elasticity as compared to the remainder of the bottom wall such that, in use, the region of increased elasticity can be freely stretched with one or more fingers of a user, thereby agitating the substance within the device.

2. The device of claim 1, wherein the bottom wall is elastic.

3. The device of claim 1, wherein the region of increased elasticity is formed a portion of the bottom wall that has a reduced thickness as compared to the remainder of the bottom wall.

4. The device of claim 1, wherein the region of increased elasticity is formed from a material that is different from the material from which the remainder of the bottom wall is formed.

5. The device of claim 1, wherein the region of increased elasticity and the remainder of the bottom wall are integrally formed.

6. The device of claim 1, wherein the bottom wall and side wall are integrally formed.

7. The device of claim 1, wherein the side wall is collapsible.

8. The device of claim 1, further comprising a member coupled to the cup-shaped body for holding the device.

9. The device of claim 1, wherein the member is a strap that is coupled to the opposing sides of the bottom wall and/or side wall and thereby passes across the outside of the bottom wall.

10. The device of claim 1, wherein the strap is sized to hold one or more fingers of a user against the bottom wall.

11. The device of claim 1, wherein the cup-shaped body is sized to cover the perineum.

12. The device of claim 1, wherein the cup-shaped body is sized to cover one of the anus and the vulva.

13. The device of claim 1, wherein the device in use does not form a seal with the perineum.

14. The device of claim 1, further comprising a handle.

15. The device of claim 12, wherein the handle is removable.

16. The device of claim 1, wherein the substance is water, lotion, cream, ointment, or paste.

17. The device of claim 14, wherein the substance is water.

18. The device of claim 1, made at least in part from an elastomeric material selected from the group consisting of silicone, polyurethane, copolymers of silicone and polyurethane, polyolefins, such as polyisobutylene and polyisoprene, neoprene, nitrile, vulcanized rubber and combinations thereof.

19. The device of claim 18, made from silicone.

20. The device of claim 1, wherein the side wall and/or the bottom wall is smooth.

* * * * *